(12) United States Patent
Alheidt et al.

(10) Patent No.: US 7,331,942 B2
(45) Date of Patent: Feb. 19, 2008

(54) FLUSH SYRINGE HAVING ANTI-REFLUX STOPPER

(75) Inventors: Thomas A. Alheidt, Stockholm, NJ (US); James John Timko, Sparta, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 670 days.

(21) Appl. No.: 10/668,725

(22) Filed: Sep. 23, 2003

(65) Prior Publication Data

US 2005/0065478 A1   Mar. 24, 2005

(51) Int. Cl.
*A61M 5/315* (2006.01)
(52) U.S. Cl. ..................................... 604/218
(58) Field of Classification Search .............. 604/187, 604/192, 201, 218, 225, 244, 256
See application file for complete search history.

(56) References Cited

U.S. PATENT DOCUMENTS

| 3,050,059 A | 8/1962 | Wall et al. |
| 4,057,052 A | 11/1977 | Kaufman et al. |
| 5,037,393 A | 8/1991 | Ellgass |
| 5,496,285 A | 3/1996 | Schumacher et al. |
| 5,795,337 A * | 8/1998 | Grimard ..................... 604/222 |
| 5,807,374 A * | 9/1998 | Caizza et al. ............... 604/411 |
| 5,899,881 A * | 5/1999 | Grimard et al. ............. 604/89 |
| 5,902,271 A | 5/1999 | Jentzen |
| 6,171,287 B1 | 1/2001 | Lynn et al. |
| 6,361,524 B1 * | 3/2002 | Odell et al. ................. 604/187 |
| 2004/0010235 A1 | 1/2004 | Weilbacher et al. ........ 604/218 |

FOREIGN PATENT DOCUMENTS

GB   2197792 A   6/1988

* cited by examiner

*Primary Examiner*—Catherine S. Williams
(74) *Attorney, Agent, or Firm*—Jeanne P. Lukasavage (57) ABSTRACT

An I.V. flush syringe assembly includes a barrel having an inside surface defining a chamber for retaining fluid, an open proximal end and a distal end including a distal wall with an elongate tip extending distally therefrom having a passageway therethrough in fluid communication with the chamber. A plunger having an elongate body portion and a stopper slidably positioned in fluid-tight engagement with the inside surface of the barrel is provided. Anti-reflux structure for controlling stopper deflection when fluid has been delivered from the chamber and the stopper is in contact with the distal wall is provided.

13 Claims, 8 Drawing Sheets

FLUSH SYRINGE HAVING ANTI-REFLUX STOPPER

BACKGROUND OF THE INVENTION

The present invention relates to syringe assemblies and particularly to syringe assemblies for use in I.V. flush procedures.

An I.V. catheter is a commonly used therapeutic device. Many patients, in accordance with their therapy, have an I.V. catheter connected to a vein ready for use in various procedures or in fluid communication with an I.V. system for infusing liquids and medication. Many I.V. sets have I.V. ports which are in fluid communication with a catheter and allow access for the purpose of injecting medication into the patient, and for use in flushing techniques to maintain catheter integrity. Healthcare facilities have flushing protocols which depend on the amount of time the catheter will remain in the patient and the type of catheter being used. For example, a peripherally inserted central catheter (PICC) is a long flexible catheter, which is typically inserted into the central venous system (optimally with the tip terminating in the superior vena cava) via the superficial veins of the antecubital fossa. PICC lines are designed for use when intermediate or long-term therapy is prescribed.

These catheter lines must be periodically flushed with saline flush solution and/or heparin lock flush solution depending on the protocol. Among other things, flushing saline solution removes blood from the catheter and heparin helps prevent the formation of future blood clots. The most common I.V. ports are covered by pierceable septums or pre-slit septums and are known in the art and sometimes referred to as "PRN" from the Latin pro re nata meaning "as the need arises". The septum is preferably made of rubber or another elastomeric material which permits insertion of a sharp needle cannula in order to infuse fluids into or to withdraw fluids from the catheter. Upon withdrawal of the needle cannula the septum seals itself. Ports having pre-slit septums are used with blunt cannula. Typically, the blunt cannula is attached to a syringe and the syringe is moved to place a gentle pressure on the pre-slit septum which is forced open by the blunt cannula to establish fluid communication. Also, some I.V. sets have access valves which are responsive to the frusto-conically shaped tip of a syringe barrel for allowing fluid communication between the interior of the syringe and the catheter without the use of a cannula.

Catheters are flushed using syringe assemblies filled with various fluids. In some cases, different fluids are injected sequentially in accordance with the protocol. For example, a saline solution followed by an anticoagulant such as heparin. The size of the syringe used to flush I.V. lines varies by various factors including the size and length of the catheter. Typically syringes of 1 ml, 3 ml, 5 ml and 10 ml volume are used.

It is important in the flush procedure not to draw blood back into the catheter where it can clot and seal the catheter, commonly referred to as "reflux". In order to prevent blood reflux into the catheter the user is encouraged to maintain a positive pressure in the line during the flush procedure. This may involve slowly withdrawing the syringe and cannula from the I.V. port while still applying pressure to the syringe plunger rod during the flush procedure. When using a syringe with an elastomeric stopper, the stopper is often compressed when it contacts the distal end of the syringe barrel at the completion of the flush procedure. When a user relieves the pressure to the plunger after the flush procedure is completed, the stopper will expand back to its normal size drawing liquid from the catheter into the syringe barrel. This is undesirable, since it can cause blood to enter the catheter at the catheter distal end (reflux). Problems with reflux of blood into the catheter are on the rise because IV lines are now being flushed by a wide variety of health care workers not just those dedicated to catheter maintenance. These other health care workers, as a result of having many other aspects of patient care to be responsible for and who spend much less time flushing IV lines, are not as efficient as those dedicated to catheter maintenance.

Therefore there is a need for simple, straight forward easy-to-manufacture syringe assemblies which helps reduce or eliminate reflux of blood into the catheter during and after the flushing procedure has occurred even if flush protocols and procedures are not precisely followed. For example, prematurely releasing the compressive force on the stopper, which may cause reflux of blood into the catheter.

SUMMARY OF THE INVENTION

The present invention is directed to a syringe assembly for use in flush applications. The syringe assembly reduces or eliminates reflux of blood into the catheter by providing a conically shaped stopper surface having a total included angle less than the angle of the conically shaped distal wall of the barrel so that the stopper seals the barrel first at its center near the passageway which discharges flush solution. Further compression of the stopper will be independent of this seal so that reflux is reduced or eliminated.

An I.V. flush syringe assembly comprises a barrel including a cylindrical sidewall having an inside surface defining a chamber for retaining fluid. The barrel includes an open proximal end and a distal end having a distal wall with an elongate tip extending distally therefrom. The tip includes a passageway therethrough in fluid communication with the chamber. The plunger having an elongate body portion includes a proximal end, a distal end and a stopper slidably positioned in fluid-tight engagement with the inside surface of the barrel for drawing fluid into and driving fluid out of the chamber by movement of the stopper relative to the barrel. The elongate body portion of the plunger extends outwardly from the open proximal end of the barrel. Anti-reflux structure is provided for controlling stopper deflection when fluid has been delivered from the chamber and the stopper is in contact with the distal wall of the barrel. Anti-reflux structure includes the stopper having a conically shaped distal surface and the barrel having a conically shaped inside surface at its distal wall. The total included angle of the inside surface of the barrel at the distal wall is greater than the total included angle of the distal surface of the stopper by at least six degrees.

In one embodiment the total included angle of the distal surface of the stopper is about 110 degrees and the total included angle of the conically shaped inside surface of the distal wall of the barrel is about 120 degrees.

The syringe assembly may further include at least one projection on the distal surface of the stopper positioned mostly in the space between the distal surface of the stopper and the conically shaped inside surface of the distal wall of the barrel when the distal surface of the stopper first contacts the conically shaped inside surface.

The syringe assembly may also include flush solution in the chamber and a tip cap releasably connected to the tip of the syringe barrel for sealing the passageway. The flush solution may be selected from the group consisting of saline flush solution and heparin lock solution.

The syringe assembly may further include a needle assembly including a cannula having a proximal end, a distal end, and a lumen therethrough. A hub having an open proximal end containing a cavity and a distal end attached to the proximal end of the cannula so that the lumen is in fluid communication with the cavity of the hub. The needle assembly is removably attached to the tip of the barrel through engagement of the tip to the cavity of the hub so that the lumen is in fluid communication with the chamber of the barrel.

Another embodiment of the I.V. flush syringe assembly of the present invention comprises a barrel including a cylindrical sidewall having an inside surface defining a chamber for retaining fluid. The barrel includes an open proximal end and a distal end having a distal wall with an elongate tip extending distally therefrom having a passageway therethrough in fluid communication with the chamber. A plunger includes an elongate body portion having a proximal end, a distal end and a stopper slidably positioned in fluid-tight engagement with the inside surface of the barrel for drawing fluid into and driving fluid out of the chamber by movement of the stopper relative to the barrel. The elongate body of the plunger extends outwardly from the open proximal end of the barrel. A tip cap is releasably connected to the elongate tip of the barrel for sealing the passageway. A quantity of flush solution is in the chamber between the stopper and the distal wall. Anti-reflux structure for controlling stopper deflection when fluid has been delivered from the chamber and the stopper is in contact with the distal wall is provided. The anti-reflux structure may include the stopper having a conically shaped distal surface and the inside surface of the barrel at the distal wall being conically shaped wherein the total included angle of the inside surface of the barrel at the distal wall is greater than the total included angle of the distal surface of the stopper by at least six degrees and preferably at least about ten degrees. At least one projection on the distal surface of the stopper is provided. The at least one projection is positioned and/or sized so that when the stopper contacts the inside surface of the barrel any deflection of the projection will not store enough energy to move the stopper proximally to the extent the stopper is disengaged from the inside surface of the distal end of the barrel near the passageway.

A method of flushing a catheter of the present invention comprises the steps of providing a syringe assembly having a barrel including a cylindrical side wall having an inside surface defining a chamber for retaining fluid, an open proximal end and a distal end including a distal wall with an elongate tip extending distally therefrom having a passageway therethrough in fluid communication with the chamber, a plunger including an elongate body portion having a proximal end, a distal end and a stopper slidably positioned in fluid-tight engagement with the inside surface of the barrel for drawing fluid into and driving fluid out of the chamber by movement of the stopper relative to the barrel, the elongate body portion extending outwardly from the open proximal end of the barrel, a quantity of flush solution in said chamber, and anti-reflux means for minimizing stopper deflection when the flush solution has been delivered from the chamber and the stopper is in contact with and pressed against the distal wall. The method further includes providing a catheter having a proximal end, a distal end and a passageway therethrough and a housing having a hollow interior in fluid communication with the passageway, the housing having an access valve capable of engaging the elongate tip of the barrel for allowing fluid communication with the hollow interior of the housing. The method further includes the steps of placing the distal end of the catheter in a blood vessel; engaging the elongate tip of the barrel with the access valve so that the passageway in the tip is in fluid communication with the hollow interior of the housing; applying force to the plunger to move the plunger in a distal direction with respect to the barrel so that the flush solution in the chamber flows through the passageway into the hollow chamber of the housing and through the passageway of the catheter; continuing to apply force to the plunger until the stopper contacts and presses against the distal wall of the barrel; and disengaging said syringe assembly from said access valve.

An alternative method may include the step of attaching a needle assembly to the elongate tip of the barrel. The needle assembly includes a cannula having a proximal end, a distal end and a lumen therethrough and a hub having an open proximal end containing a cavity and a distal end attached to the proximal end of the cannula so that the lumen is in fluid communication with the cavity. The attachment of the needle assembly to the barrel is through frictional engagement between the cavity in the hub and the elongate tip. This alternative method is used with a catheter having a proximal end, a distal end and a passageway therethrough and a housing having a hollow interior connected to the catheter and in fluid communication with the passageway of the catheter. The housing further includes a septum for allowing fluid communication with the hollow interior. Fluid communication is established by forcing the distal end of the cannula through the septum so that the lumen of the cannula is in fluid communication with the hollow interior of the housing. Also, the cannula may be permanently attached to the barrel tip with or without the use of a hub. At completion of the flush procedure the cannula is withdrawn from the septum.

DETAILED DESCRIPTION

Figure 1:
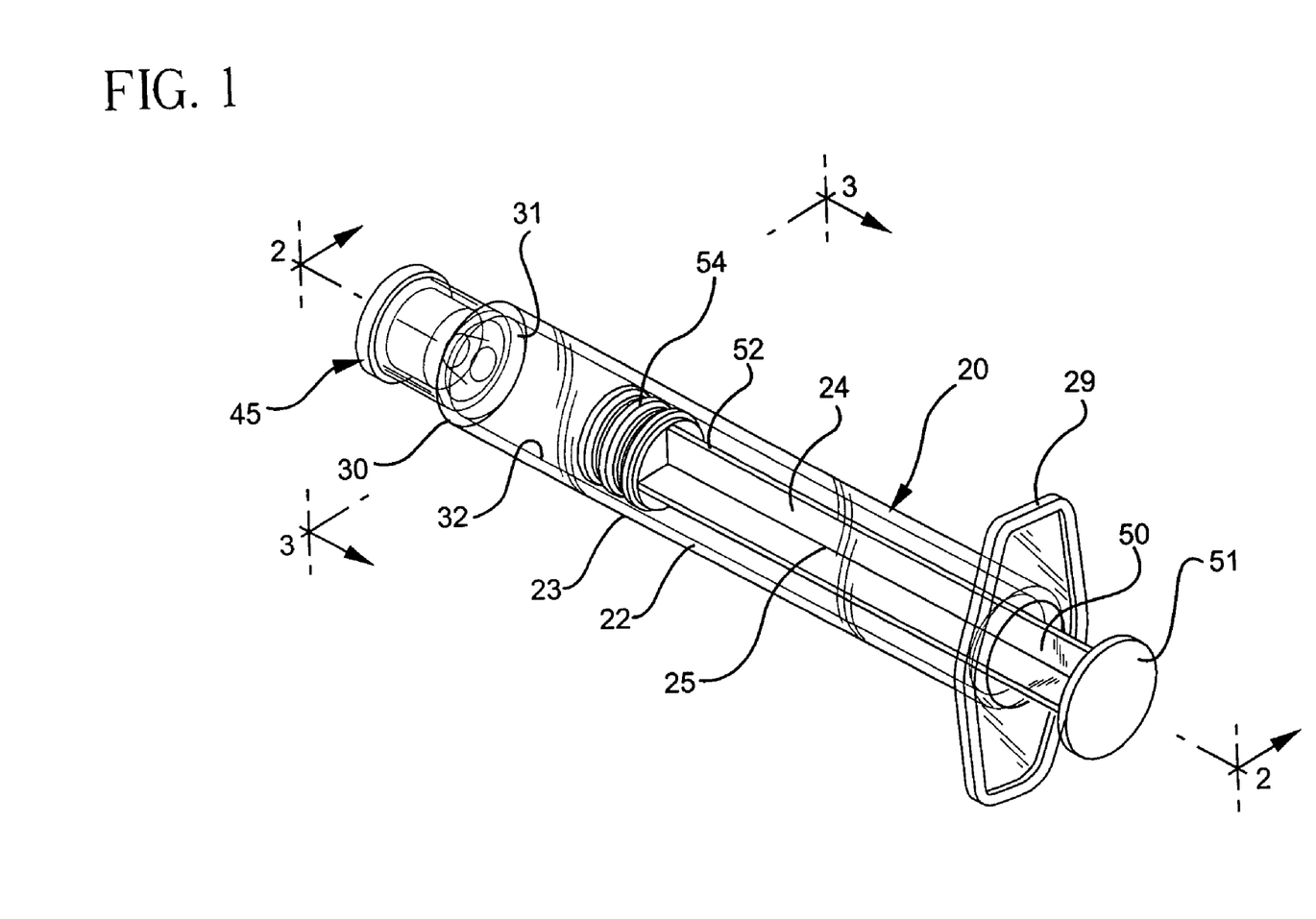
FIG. 1 is a perspective view of a syringe assembly according to one embodiment of the invention.
Figure 2:
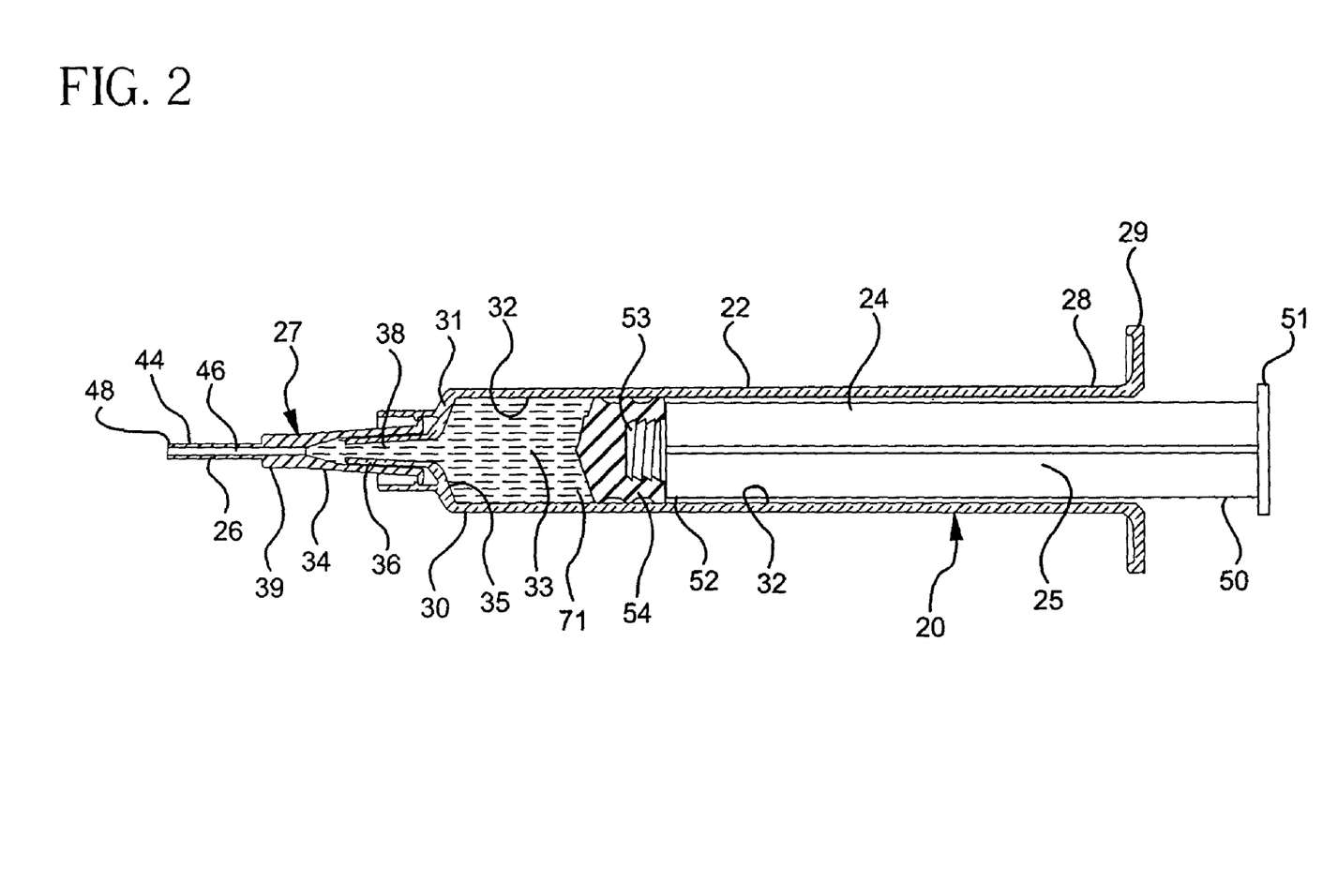
FIG. 2 is a partially cross-sectioned side elevational view of the syringe assembly of FIG. 1 with a needle assembly attached.
Figure 3:
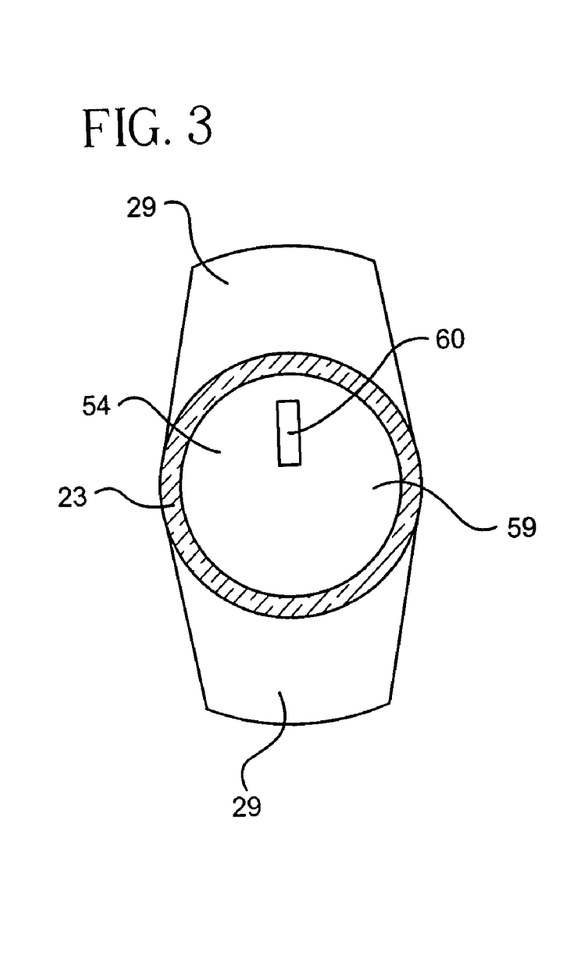
FIG. 3 is a cross-sectional view of the syringe assembly of FIG. 1 taken along line 3-3.
Figure 4:
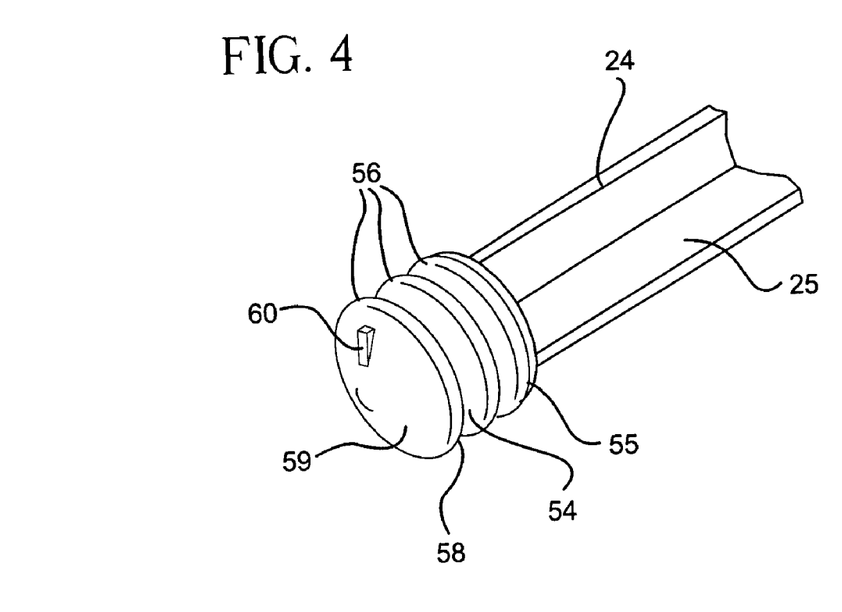
FIG. 4 is a partial perspective view of the stopper and distal end of the plunger of the syringe assembly of FIG. 1.
Figure 5:
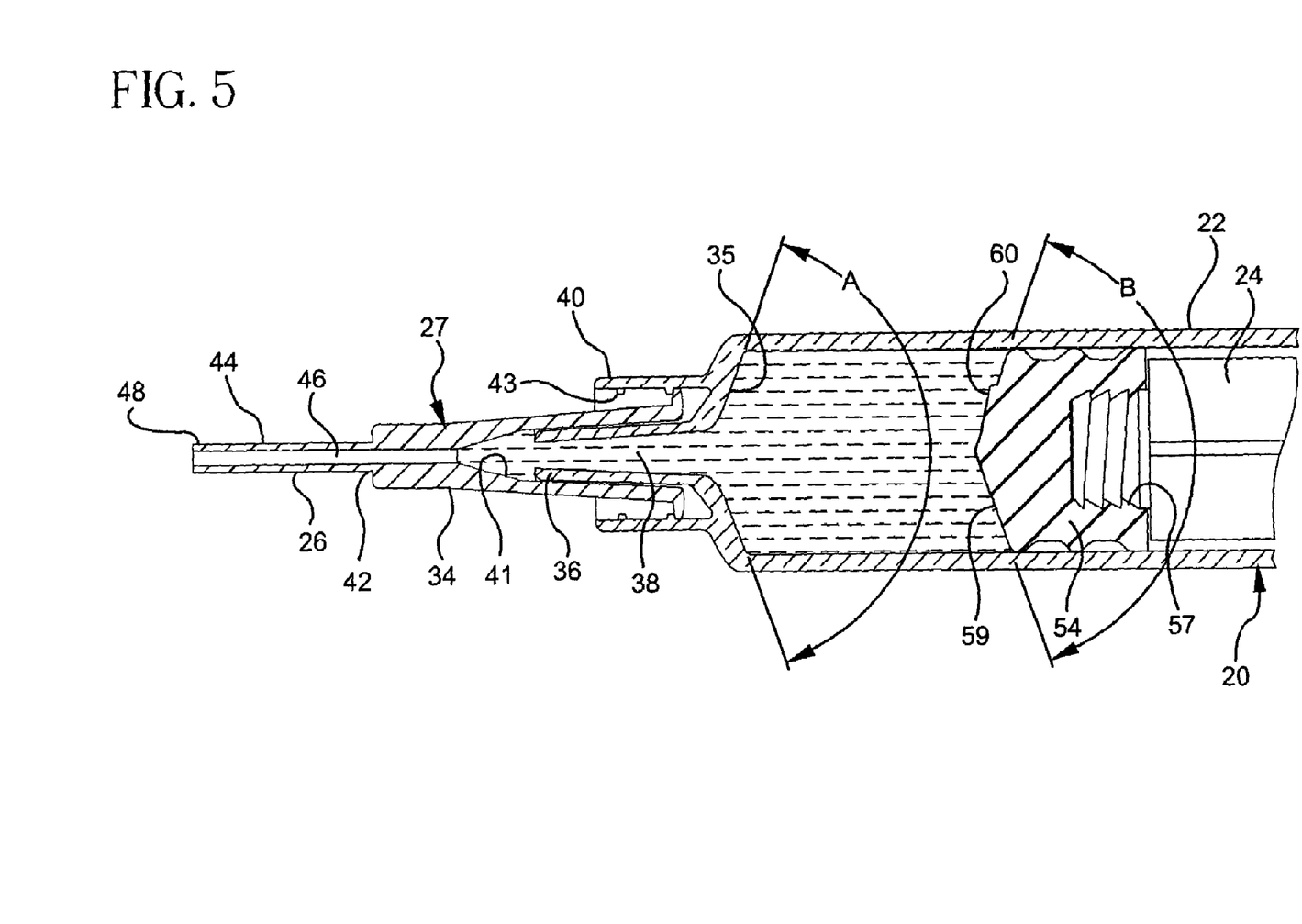
FIG. 5 is an enlarged partial cross-sectional side elevation view of the distal end of the syringe assembly of FIG. 2.
Figure 6:
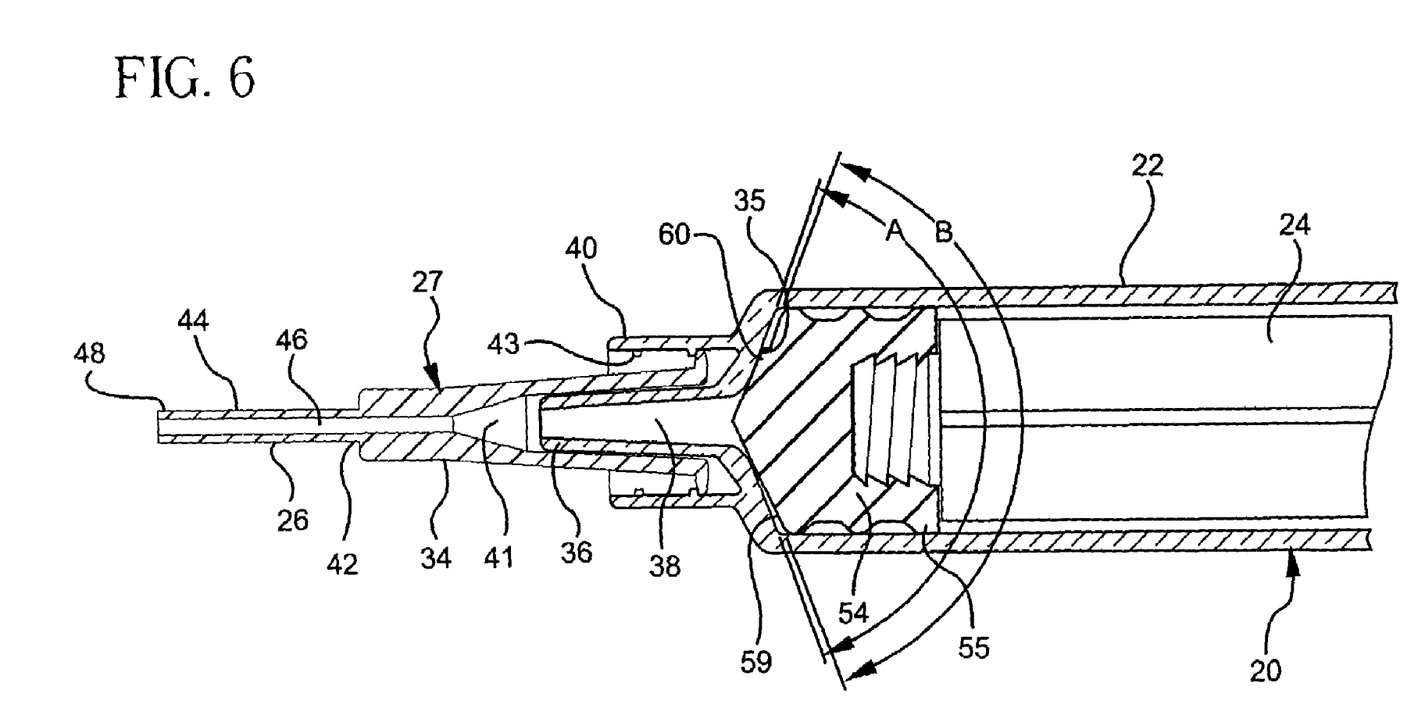
FIG. 6 is an enlarged partial cross-sectional side elevational view of the distal end of the syringe assembly shown at the completion of a flush procedure.

FIG. 1 shows a syringe 20 according to the present invention generally comprising a barrel 22 and a plunger 24. The barrel 22 has a generally cylindrical side wall 23 including an open proximal end 28 having finger grips 29, a distal end 30 having a distal wall 31 and an inside surface 32 defining a chamber 33 for retaining fluid. The inside surface of the barrel at the distal wall is conically shaped as indicated as numeral 35. The conically shaped inside surface of the distal wall of the barrel has a total included angle A as illustrated in FIG. 5. Distal end 30 further includes a tip 36 having a passageway 38 in fluid communication with the chamber. The distal end of barrel 22 preferably, but not necessarily includes a locking luer type collar 40 concentrically surrounding tip 36. The inside surface of the collar includes at least one thread 43. A cannula 26 includes a proximal end 42, a distal end 44 and a lumen 46 therethrough. The distal end may include a sharp tip or a blunt tip 48 as shown. The cannula may be connected directly to the tip of the syringe barrel to establish fluid communication between the lumen and the chamber. Also, the cannula may be part of a needle assembly 27 including a hub 34 having an open proximal end 37 containing a cavity 41 and a distal end 39 attached to the proximal end of the cannula so that the lumen of the cannula is in fluid communication with the cavity. The cavity of the hub can be removably frictionally engaged to the tip of the barrel as illustrated in FIGS. 2, 5 and 6.

Plunger 24 includes an elongate body portion 25, a proximal end 50 having a flange 51, and a distal end 52. A stopper 54 is disposed on projection 53 at distal end 52 of the plunger, preferably via threading engagement. Stopper 54 includes at least one rib and preferably a plurality of ribs 56 on its outside diameter. The stopper is slidably positioned in fluid-tight engagement with the inside surface of the barrel for drawing fluid into and drawing fluid out of the chamber, through the passageway, by movement of the stopper relative to the barrel. Stopper 54 includes a proximal end 55 having a cavity 57 therein for engaging projection 53 on the distal end 52 of the plunger. Stopper 54 further includes a distal end 58 having a conically shaped distal surface 59 thereon. Conically shaped distal surface 59 has a total included angle B as illustrated in FIG. 5. As will be explained in more detail hereinafter total included angle A of the inside surface of the barrel at the distal wall is greater than total included angle B of the conically shaped distal surface of the stopper. Angle A is at least six degrees, and preferably at least about ten degrees more than angle B. In this preferred embodiment, angle A is about 120 degrees and angle B is about 110 degrees.

Stopper 54 preferably includes at least one projection or lug 60 on conically shaped distal surface 59. Projection 60 keeps the stoppers from nesting or sticking to each other during the assembly process. For example, the conically shaped distal surface of one stopper may position itself in the cavity of another stopper while the stoppers are together before assembly.

The stopper may be made of any material suitable for providing sealing characteristics while under compression. For example, the stopper may be made of thermoplastic elastomers, natural rubber, synthetic rubber or thermoplastic materials and combinations thereof. The plunger in this embodiment is preferably made of material which is more rigid than the stopper such as polypropylene, polyethylene and the like.

In operation, syringe 20 is connected to a needle assembly and filled with flush solution using known methods. The flush solution may be any solution intended for flushing. It is preferred that the flush solution be selected from the group consisting of saline flush solution and heparin lock flush solution. These solutions are known in the art and readily available. An example of a saline flush solution is 0.9% Sodium Chloride USP. An example of a heparin lock flush solution is 0.9% Sodium Chloride with 100 USP units of Heparin Sodium per ml or 10 USP units of Heparin Sodium per ml. The syringe with needle assembly attached is used to pierce the pierceable septum or a blunt cannula may be inserted into a pre-split septum of a vial containing flush solution and the flush solution is drawn into the syringe barrel by pulling plunger rod flange 51 in the proximal direction while holding barrel 22, to draw fluid through the needle cannula into fluid chamber 33.

Alternatively, the syringe may be filled with flush solution during the manufacturing of the syringe via a sterile filling method. Such prefilled syringes may be supplied with a tip cap, such as tip cap 45 releasably connected to tip 36 sealing passageway 38. It is preferred that the tip cap is formed of material selected from the group of thermoplastic materials and elastomeric materials such as natural and synthetic rubber and thermoplastic elastomers.

Figure 7:
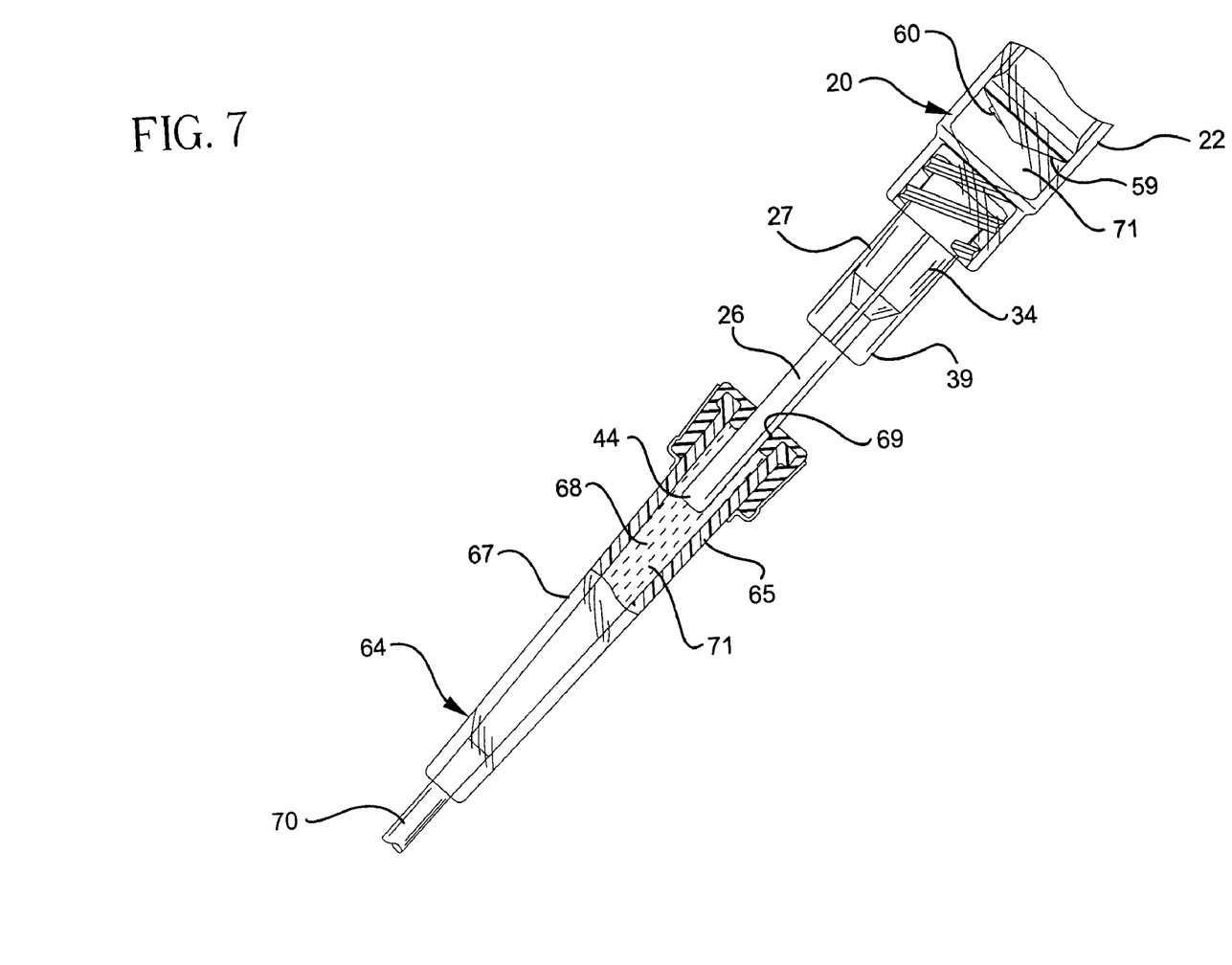
FIG. 7 is a side-elevational view illustrating the syringe assembly in use with a catheter injection site.

The syringe is now ready for use in flushing a catheter of an I.V. set. I.V. sets can be very complicated and may include multiple injection ports, a valve and/or other components. For the purpose of illustrating the present invention a simplified I.V. set 64 is illustrated in FIG. 7. I.V. set 64 comprises an I.V. site 65 which includes a housing 67 having a hollow interior 68 and a septum 69 at its proximal end. A catheter 70 having a conduit therethrough extends from the distal end of the housing. For this I.V. set septum 69 is pre-slit for use with blunt cannula. The I.V. site may be a valve having structure for accepting the syringe barrel tip and being activated by the insertion of the tip to establish fluid communication with the catheter, such as the valve taught in U.S. Pat. No. 6,171,287.

Blunt tip 48 of cannula 26 may be inserted through pre-split septum 69 of I.V. set 64. Alternatively, a sharp tip of a needle cannula may be used to pierce a septum that is not pre-split, or the tip of the barrel may be engaged with a valve in the IV site. This establishes fluid communication between the interior 68 of the I.V. set and the chamber of the syringe barrel. The syringe barrel 22 is preferably held via finger grips 29. Pressure is then applied to flange 51 of the plunger, for example by a thumb, in the distal direction. This moves the plunger 24 having the stopper 54 on its distal end forcing the liquid such as flush solution 71 in the chamber 34 out of the chamber, through cannula 26 and into interior 68 of the I.V. set and then through catheter 70.

Referring to FIG. 6 the position of the plunger and stopper at the completion of the flush procedure is shown. At the completion of the flush procedure conically shaped distal surface 59 of the stopper contacts conically shaped inside surface 35 of the distal end wall of the barrel near passageway 30 sealing the passageway so that further deflection of the stopper will have little or no effect on liquid in the passageway and the catheter. Accordingly, stopper deflection caused by additional unnecessary force applied to the plunger, at this time, which could cause reflux of blood into the catheter using prior art stoppers, is minimized or eliminated with the stopper of the present invention. The stopper may flex, however, this flexure will occur generally outside of the sealed area surrounding the entrance to the passageway. Further, projection 60 is shaped so that upon further deflection of the stopper through forces applied to the plunger, the projection will not be able to force the stopper to move proximally. That is, the projection cannot create enough force to move the stopper proximally to create reflux. It is preferred that the projection on the distal surface of the stopper be positioned mostly in space 61 between the conically shaped distal surface of the stopper and the conically shaped inside surface of the distal wall of the barrel as illustrated in FIG. 6. The projection should be sized and positioned so that it cannot absorb enough energy during deflection to move the stopper proximally and break the seal between the stopper and the barrel at the passageway. The projection can be angularly shaped having a distal surface at the same angle as inside surface 35 of the barrel as illustrated in FIG. 6.

Figure 8:
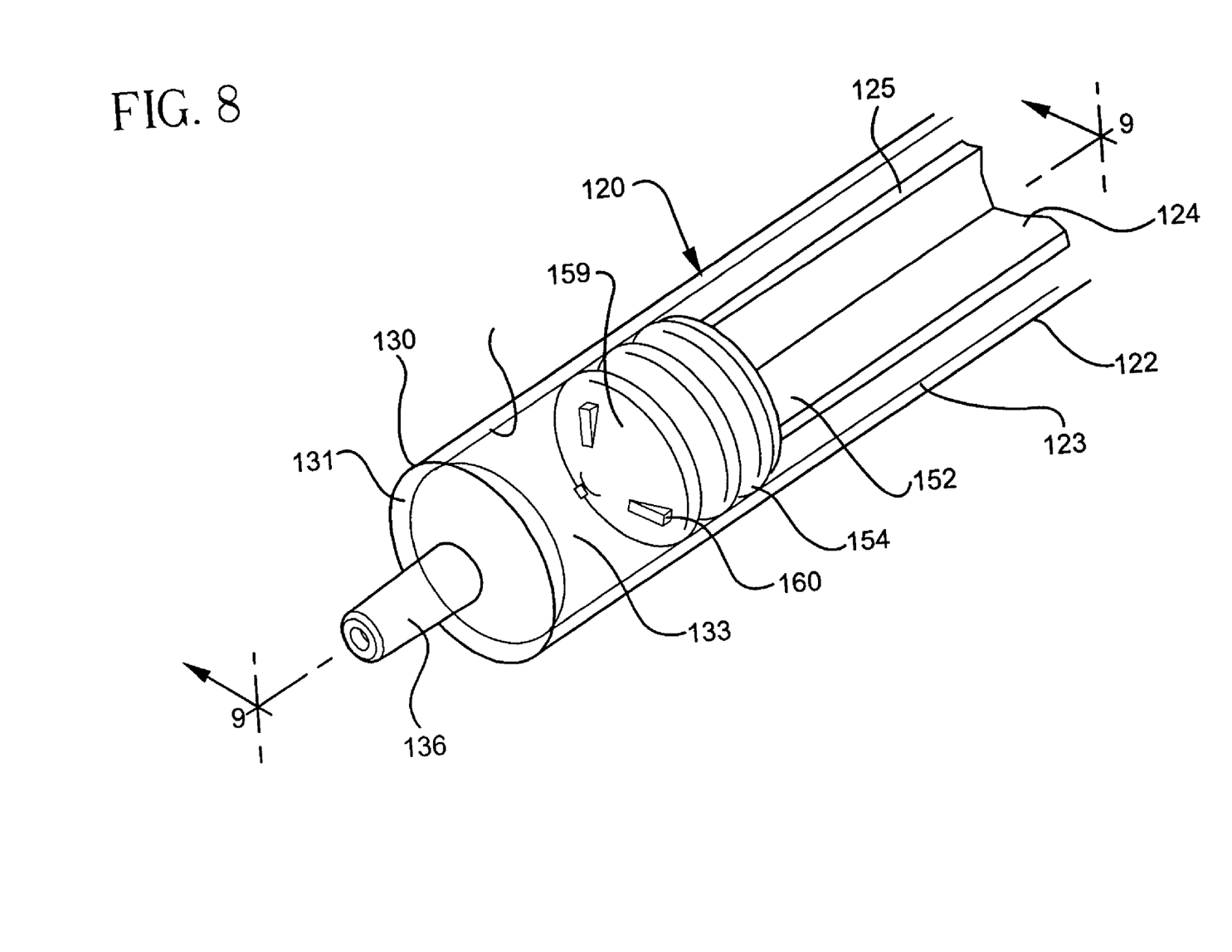
FIG. 8 is a perspective view of a syringe assembly according to another embodiment of the invention.
Figure 9:
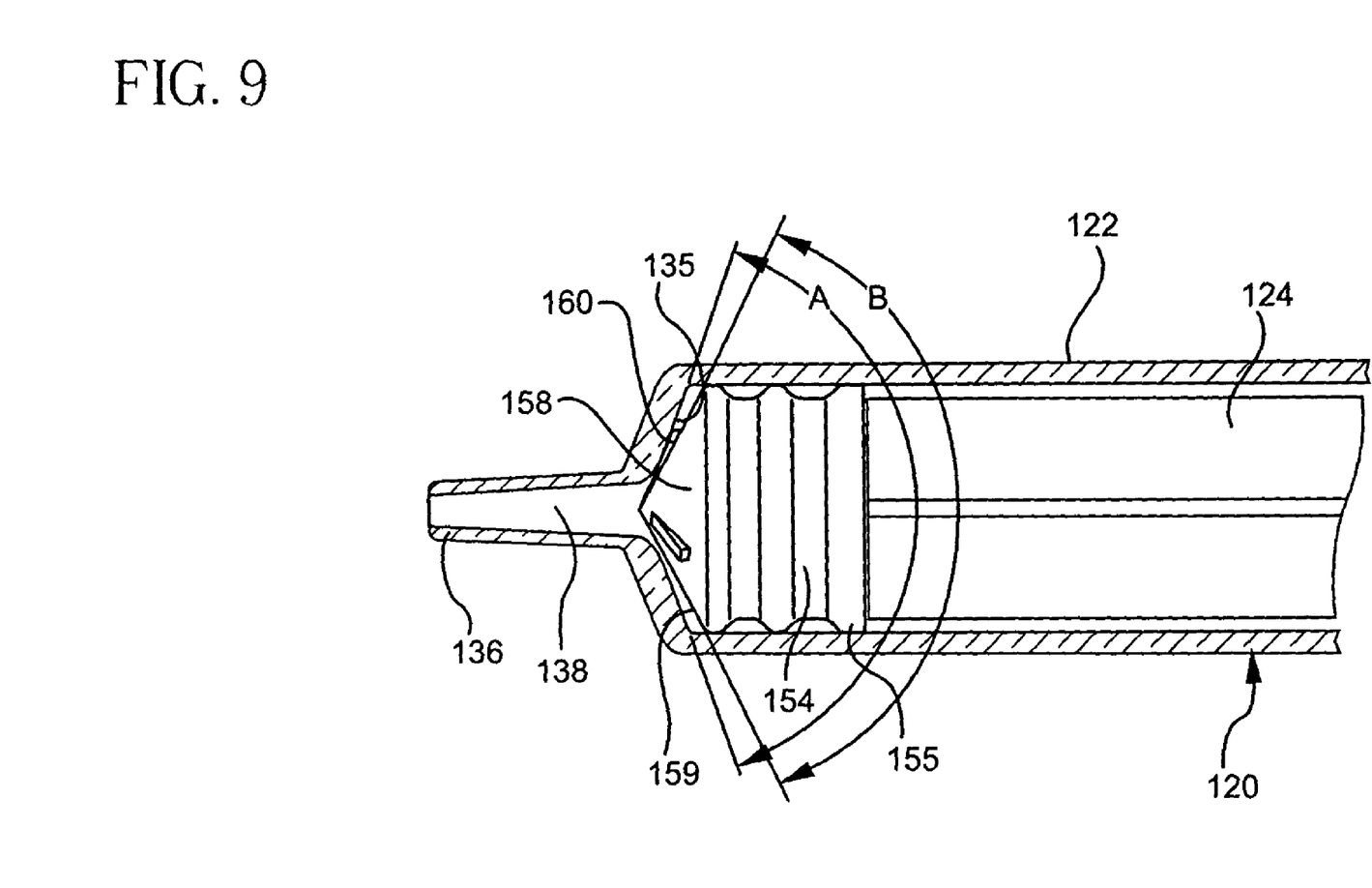
FIG. 9 is partially cross-sectioned perspective view of the syringe assembly of FIG. 8, taken along line 9-9.

FIGS. 8 and 9 illustrate an alternative embodiment of the syringe assembly of the present invention. In this embodiment syringe assembly 120 comprises a barrel 122 including a cylindrical sidewall 123 having an inside surface 132 defining a chamber 133 for retaining fluid. Distal end 130 of the barrel includes a distal wall 131 having an elongate tip 136 extending distally therefrom. The tip includes passageway 138 which is in fluid communication with the chamber. The distal wall includes conically shaped inside surface 135.

A plunger 124 includes an elongate body portion 125 having a distal end 152 and a resilient stopper 154 slidably positioned in fluid-tight engagement with the inside surface of the barrel. The stopper includes at least one rib 156 and a conically shaped distal surface 159 at distal end 158. The total included angle of the conically shaped inside surface A of distal wall 131 is greater than conically shaped distal surface B on the stopper by at least eight degrees. In this embodiment the difference between angle A and angle B is about 20 degrees.

The distal surface of the stopper includes a plurality of projections or lugs 160 which are sized and positioned not to interfere with the sealing action of the conically shaped distal surface of the stopper as it contacts the conically shaped inside surface of the distal wall of the barrel. Further, the projections should be positioned such that and/or structured so that when they are in a partially compressed state they are not alone capable of forcing the stopper proximally in the barrel to disengage the seal between the conically shaped distal surface of the stopper and the barrel near the passageway.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as disclosed.

What is claimed is:

1. An I.V. flush syringe assembly comprising:
   a barrel including a cylindrical side wall having an inside surface defining a chamber for retaining fluid, an open proximal end and a distal end including a distal wall with an elongate tip extending distally therefrom having a passageway therethrough in fluid communication with said chamber;
   a plunger including an elongate body portion having a proximal end, a distal end and a stopper slidably positioned in fluid-tight engagement with said inside surface of said barrel for drawing fluid into and driving fluid out of said chamber by movement of said stopper relative to said barrel, said elongate body portion extending outwardly from said open proximal end of said barrel; and
   anti-reflux means comprising said stopper having a conically shaped distal surface and said inside surface of said barrel at said distal wall being conically shaped wherein a total included angle of said inside surface of said barrel at said distal wall is greater than a total included angle of said stopper distal surface by at least 6°, wherein upon delivery of fluid from said chamber, said stopper contacts the distal end of the barrel and seals said passageway so that stopper deflection is controlled.

2. The syringe assembly of claim 1 wherein said total included angle of said stopper distal surface is about 110°.

3. The syringe assembly of claim 1 wherein the total included angle conically shaped inside surface of said distal wall of said barrel is about 120°.

4. The syringe assembly of claim 1 further including at least one projection on said distal surface of said stopper positioned mostly in a space between said distal surface and said conically shaped inside surface of said distal wall when said distal surface of said stopper first contacts said conically shaped inside surface.

5. The syringe assembly of claim 1 including flush solution in said chamber.

6. The syringe assembly of claim 5 further including a tip cap releasably connected to said tip of said syringe barrel for sealing said passageway.

7. The syringe assembly of claim 5 wherein said flush solution is selected from the group consisting of saline flush solution and heparin lock flush solution.

8. The syringe assembly of claim 1 wherein said stopper is made of material selected from the list consisting of thermoplastic elastomers, natural rubber, synthetic rubber, thermoplastic materials and combinations thereof.

9. The syringe assembly of claim 1 further comprising a needle assembly including a cannula having a proximal end, a distal end and a lumen therethrough, and a hub having an open proximal end containing a cavity and a distal end attached to said proximal end of said cannula so that said lumen is in fluid communication with said cavity, said needle assembly being removably attached to said tip of said barrel through engagement of said tip to said cavity so that said lumen is in fluid communication with said chamber.

10. An I.V. flush syringe assembly comprising:
   a barrel including a cylindrical side wall having an inside surface defining a chamber for retaining fluid, an open proximal end and a distal end including a distal wall with an elongate tip extending distally therefrom having a passageway therethrough in fluid communication with said chamber;
   a plunger including an elongate body portion having a proximal end, a distal end and a stopper slidably positioned in fluid-tight engagement with said inside surface of said barrel for drawing fluid into and driving fluid out of said chamber by movement of said stopper relative to said barrel, said elongate body portion extending outwardly from said open proximal end of said barrel; and
   a tip cap releasably connected to said tip of said syringe barrel for sealing said passageway;
   a quantity of flush solution in said chamber between said stopper anti said distal wall; anti-reflux means for controlling stopper deflection when fluid has been delivered from said chamber and said stopper is in contact with said distal wall, said anti-reflux means including said stopper having a conically shaped distal surface and said inside surface of said barrel at said distal wall being conically shaped wherein a total included angle of said inside surface of said barrel at said distal wall being greater Than a total included angle of said distal surface of said stopper by at least 6° so that said stopper seals said passageway when said stopper contacts said distal wall; and at least one projection on said distal surface of said stopper, said at least one projection having a distal surface the same angle as said distal surface of said inside surface of said barrel and positioned mostly in the space between said distal surface and said conically shaped inside surface of said distal wall when said distal surface first contacts said conically shaped inside surface.

11. The IV. flush syringe assembly of claim 10, wherein said at least one projection is positioned away from the center of said distal surface of said stopper so that said at least one projection does not interfere with the seal created when said stopper contacts said distal wall of said barrel.

12. A method of flushing a catheter comprising the steps of:
(a) providing a syringe assembly having a barrel including a cylindrical side wall having an inside surface defining a chamber for retaining fluid, an open proximal end and a distal end including a distal wall with an elongate tip extending distally therefrom having a passageway therethrough in fluid communication with said chamber, a plunger including an elongate body portion having a proximal end, a distal end, and a stopper slidably positioned in fluid-tight engagement with said inside surface of said barrel for drawing fluid into and driving fluid out of said chamber by movement of said stopper relative to said barrel, said elongate body portion extending outwardly from said open proximal end of said barrel, a quantity of flush solution in said chamber, and anti-reflux means comprising said stopper having a conically shaped distal surface and said inside surface of said barrel at said distal wall being conically shaped wherein said total included angle of said inside surface of said barrel at said distal wall is greater than said total included angle of said stopper distal surface by at least 6°, for controlling stopper deflection when said flush solution has been delivered from said chamber and said stopper is in contact with said distal wall;
(b) providing a catheter having a proximal end, a distal end a passageway therethrough and a housing having a hollow interior connected to said catheter and in fluid communication with said passageway, said housing having an access valve for allowing fluid communication with said hollow interior;
(c) placing said distal end of said catheter in a blood vessel;
(d) engaging said elongate tip of said barrel with said access valve so that said passageway of said syringe barrel is in fluid communication with said hollow interior of said housing;
(e) applying farce to said plunger to move said plunger in a distal direction with respect to said barrel so that said flush solution in said chamber flows through said passageway into said hollow chamber of said housing and through said passageway of said catheter;
(f) continue applying force to the plunger until said stopper contacts and presses against said distal wall of said barrel forming a seal around said passageway; and
(g) disengaging said elongate tip from said access valve.

13. A method of flushing a catheter comprising the steps of:
(a) providing a syringe assembly having a barrel including a cylindrical sidewall including an inside surface defining a chamber for retaining fluid, an open proximal end and a distal end including a distal wall with an elongate tip extending distally therefrom having a passageway therethrough in fluid communication with said chamber, a plunger including an elongate body portion having a proximal end, a distal end, and a stopper slidably positioned in fluid-tight engagement with said inside surface of said barrel for drawing fluid into and driving fluid out of said chamber by movement of the stopper relative to said barrel, said elongate body portion extending outwardly from said open proximal end of said barrel, a quantity of flush solution in said chamber, a needle assembly including a cannula having a proximal end, a distal end and a lumen therethrough and a hub having an open proximal end containing a cavity and a distal end attached to said proximal end of said cannula so that said lumen is in fluid communication with said cavity, said needle assembly being attached to said tip of said barrel so that said lumen is in fluid communication with said chamber, and anti-reflux means comprising said stopper having a conically shaped distal surface and said inside surface of said barrel at said distal wall being conically shaped wherein said total included angle of said inside surface of said barrel at said distal wall is greater than said total included angle of said stopper distal surface by at least 6°, for controlling stopper deflection when said flush solution has been delivered from said chamber and said stopper is in contact with said distal wall;
(b) providing a catheter having a proximal end, a distal end and a passageway therethrough and a housing having a hollow interior connected to said catheter and in fluid communication with said passageway, said housing having a septum for allowing fluid communication with said hollow interior;
(c) placing said distal end of said catheter in a blood vessel;
(d) forcing said distal end of said cannula through said septum so that said lumen is in fluid communication with said hollow interior of said housing;
(e) applying force to said plunger to move said plunger in a distal direction with respect to said barrel so that said flush solution in said chamber flows through said passageway into said hollow chamber of said housing and through said passageway of said catheter;
(f) continue applying force to the plunger until said stopper contacts and presses against said distal wall of said barrel, forming a seal around said passageway; and
(g) withdrawing said cannula from said septum.

* * * * *

UNITED STATES PATENT AND TRADEMARK OFFICE
CERTIFICATE OF CORRECTION

PATENT NO.         : 7,331,942 B2
APPLICATION NO. : 10/668725
DATED                 : February 19, 2008
INVENTOR(S)        : Thomas A. Alheidt et al.

It is certified that error appears in the above-identified patent and that said Letters Patent is hereby corrected as shown below:

Claim 10, column 8, line 64: "stopper anti said distal wall" should be "stopper and said distal wall"

Claim 12, column 9, line 59: "applying farce to said plunger" should be "applying force to said plunger"

Signed and Sealed this

Twenty-second Day of December, 2009

David J. Kappos
*Director of the United States Patent and Trademark Office*